United States Patent [19]

Yamamoto

[11] Patent Number: 5,043,464

[45] Date of Patent: Aug. 27, 1991

[54] FLUORINE-CONTAINING SURFACTANT AND PROCESS FOR PRODUCING THE SAME

[75] Inventor: Yasushi Yamamoto, Takasaki, Japan

[73] Assignee: Shin-Etsu Chemical Co., Ltd., Tokyo, Japan

[21] Appl. No.: 513,890

[22] Filed: Apr. 24, 1990

[30] Foreign Application Priority Data

Apr. 25, 1989 [JP] Japan .................... 1-105373

[51] Int. Cl.$^5$ .......................... C07F 7/08; C07F 7/18
[52] U.S. Cl. ..................................... 556/437; 556/448
[58] Field of Search ............................... 556/448, 437

[56] References Cited

U.S. PATENT DOCUMENTS

| | | | |
|---|---|---|---|
| 2,759,019 | 8/1956 | Brown et al. | 260/556 |
| 3,639,156 | 2/1972 | Pittman et al. | 556/448 X |
| 3,809,783 | 5/1974 | Pittman et al. | 556/448 X |
| 4,895,966 | 1/1990 | Kubota et al. | 556/448 |
| 4,968,828 | 11/1990 | Yamamoto | 556/448 |

FOREIGN PATENT DOCUMENTS

| | | | |
|---|---|---|---|
| 1768630 | 7/1971 | Fed. Rep. of Germany | 556/448 X |
| 59-1319 | 1/1959 | Japan | 556/448 X |

*Primary Examiner*—Paul F. Shaver

*Attorney, Agent, or Firm*—Oblon, Spivak, McClelland, Maier & Neustadt

[57] ABSTRACT

The fluorine-surfactant of the present invention has a fluorine-containing group and a hydrophilic polyether group bonded to each other through a silicon atom, and this is obtained by reacting an organosilicon compound of the formula:

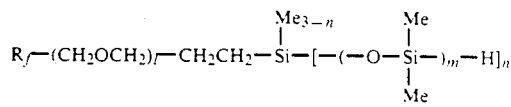

wherein $R_f$ is a fluorine-containing organic group, l and m are each an integer of 0 or 1, and n is an integer of 1 to 3, with a polyether compound represented by the formula:

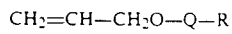

wherein Q is a polyether group, and R is either a hydrogen atom, the allyl group or an acyl group, in the presence of a platinum catalyst.

4 Claims, No Drawings

FLUORINE-CONTAINING SURFACTANT AND PROCESS FOR PRODUCING THE SAME

BACKGROUND OF THE INVENTION

1. Field of the Invention

This invention relates to a novel fluorine-containing surfactant and a process for producing the same.

2. Description of the Prior Art

Heretofore, as fluorine-containing surfactants, there have been known those prepared by use of perfluoroalkylsulfonyl fluoride ($C_8F_{17}SO_2F$), perfluoroalkylcarbonly fluoride ($C_7F_{15}COF$), etc. obtained by electrolytic fluorination as a starting material and by bonding a polyether group to these through an amide group or an ester group. However, in such reaction, there is involved the problem that the yield of perfluoroalkyl derivatives with 6 or more carbon atoms useful as surfactants is very low. Further, there is also the problem that esters of carboxylic acids having perfluoroalkyl groups ($C_7F_{15}COOR$) are susceptible to hydrolysis and unstable.

On the other hand, polyether surfactants obtained by the reaction of ethylene oxide with perfluoroalkylcarbinol have been well known in the art, but because the polymerization degree of ethylene oxide can be controlled with difficulty, it is not a satisfactory production process.

Accordingly, there has been developed a process which comprises allowing dimer to tetramer oligomers of hexafluoropropylene (HFP) to react with terminal hydroxy groups of polyether (see Japanese Patent Publication (KOKOKU) No. 1319/1984). However, HFP oligomers contain several kinds of isomers mixed therein, and since addition of hydroxyl groups of the polyether may not sometimes proceed depending on the structure of such isomers, there is the problem that the reaction efficiency is low.

Further, there has been proposed a process for producing a surfactant which comprises reacting an epoxide having a fluorine-containing organic group

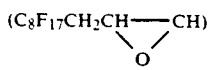

with a polyether having hydroxyl groups at terminal ends (see Japanese Pre-examination Patent Publication (KOKAI) No. 133244/1986), but in this case, in addition to the high cost of starting materials, the epoxy ring of the epoxide is unstable, and the process is not advantageous also from the viewpoint of reaction efficiency.

SUMMARY OF THE INVENTION

Accordingly, an object of the present invention is to provide a novel fluorine-containing surfactant, and a process capable of producing the fluorine-containing surfactant by use of starting materials excellent in stability and at high reaction efficiency.

Thus, according to the present invention, there is provided a fluorine-containing surfactant essentially consisting of at least one compound selected from the group consisting of:

fluorine-containing silicon compounds of the formula [I]:

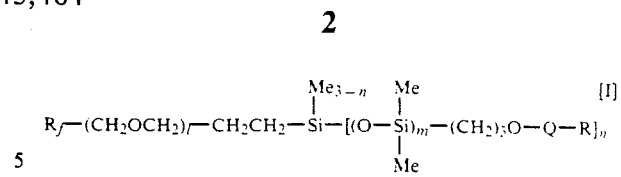

wherein $R_f$ represents a perfluoroalkyl group having 4 to 10 carbon atoms or a perfluoropolyether group having 5 to 14 carbon atoms;

Q represents a polyether group consisting of a polyethylene glycol chain, a polypropylene glycol chain or an admixture thereof;

R represents a hydrogen atom, the allyl group, an alkyl group having 1 to 4 carbon atoms, or an acyl group having 2 to 3 carbon atoms;

l and m are each an integer of 0 or 1, and n is an integer of 1 to 3, and fluorine-containing silicon compounds of the formula [II]:

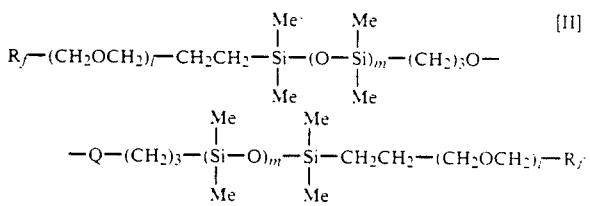

wherein Rf, Q, l and m are the same as defined above.

According to the present invention, there is further provided a process for producing the fluorine-containing surfactant, which comprises reacting:

(A) an organosilicon compound represented by the formula [III]:

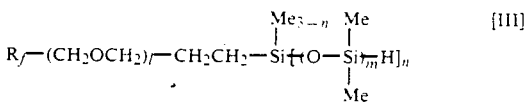

wherein $R_f$, l and m are the same as defined above, with (B) a polyether compound represented by the formula [IV]:

$$CH_2=CH-CH_2O-Q-R \quad [IV]$$

wherein Q and R are the same as defined above, in the presence of a platinum catalyst.

The process for producing the fluorine-containing surfactant of the present invention has a specific feature in use of an organosilicon compound (A) having a fluorine-containing organic group and a polyether compound (B) having an allyl group at one end in combination as starting materials. The process produces a fluorine-containing surfactant having a hydrophobic fluorine-containing organic group and a hydrophilic polyether group bonded to each other through a silicon atom by carrying out the hydrosilylation reaction between the active Si—H group of the organosilicon compound (A) and the allyl group of the polyether compound (B) in the presence of a platinum catalyst. Such production process has the advantages that the starting materials used have high chemical stability, and also that the reaction efficiency of the synthetic reaction by use of these starting materials is extremely high.

The fluorine-containing surfactant produced according to this process has the properties of imparting or improving such characteristics as wettability, penetrability, spreadability, foam stability, flowability, emulsifiability, dispersibility, water repellency, oil repellency, etc., and applicable in various fields such as plastic and rubber industries, petrochemical industries, textile industries, etc.

DETAILED DESCRIPTION OF THE INVENTION

(A) Organosilicon compound

The organosilicon compound (A) to be used as one of the starting materials in the production process of the present invention is represented by the above formula [III], namely:

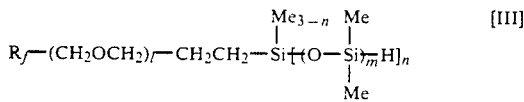

wherein $R_f$, l and n are the same as defined above.

Here, the fluorine-containing organic group $R_f$ is one to be introduced as the hydrophobic group for having the surfactant exhibit hydrophobic nature, and it is a perfluoroalkyl group having 4 to 10 carbon atoms or a perfluoropolyether group having 5 to 14 carbon atoms.

Such a perfluoroalkyl group is represented by the following formula:

$C_kF_{2k+1}-$ where k is an integer of 4 to 10, including specifically nonafluorobutyl, undecafluoropentyl, tridecafluorohexyl, pentadecafluoroheptyl, heptadecafluorooctyl, nonadecafluorononyl, heneicosafluorodecyl, 7-trifluoromethylhexadecafluorooctyl, 5-trifluoromethyldodecafluorohexyl groups, etc. Among these perfluoroalkyl groups, typical ones are those having 4, 6 and 8 carbon atoms. Where the fluorine-containing organic group $R_f$ is the perfluoroalkyl group as described above, the symbol l in the formula [III] is preferably 0, and the organosilicon compound (A) in this case is represented by the following formula [IIIa]:

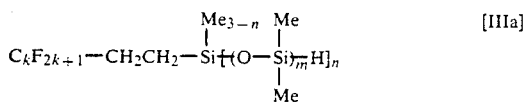

wherein k, m and n are the same as defined above.

The perfluoroalkylether group having 5 to 14 carbon atoms includes, for example, those represented by the following formula:

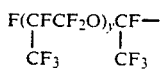

wherein y is an integer of 1 to 4. Where the fluorine-containing organic group $R_f$ is such perfluoroalkyl groups, the symbol l in the above formula [III] is preferable 1, and the organosilicon compound (A) in this case is represented by the following formula [IIIb]:

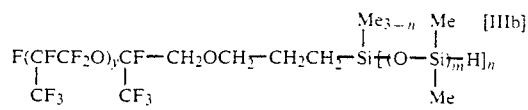

wherein y, m and n are the same as defined above.

Examples of such perfluoroalkylether groups may be represented by the formula $R_fCH_2OCH_2-$, namely:

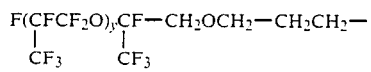

wherein y is an integer of 1 to 4 as defined above, including specifically 6-trifluoromethyl-6,8,8,9,9,9,10,10,10-octafluoro-4,7-dioxadecyl, 6,9-bis(trifluoromethyl)-6,8,8,9,11,11,12,12,13,13,13,undecafluoro-4,7,10-trioxatridecyl, 6,9,12-tris(trifluoromethyl)-6,8,8,9,11,11,12,14,14,15,15,16,16,16,-tetradecafluoro-4,7,10,13-tetraoxadecyl groups, etc.

The organosilicon compound (A) represented by the formula [III] can be prepared according to, for example, the method as described below.

That is, the organosilicon compound of the above formula [III] wherein m is 0 can be prepared, for instance, in the case n=1, by reducing a monochlorosilane having the molecular structure corresponding thereto with a metal hydride as shown by the following reaction scheme (i) (see W. H. Hebergall, O. H. Johnson, J. Am. Chem. Soc., 71, 4022 (1949)):

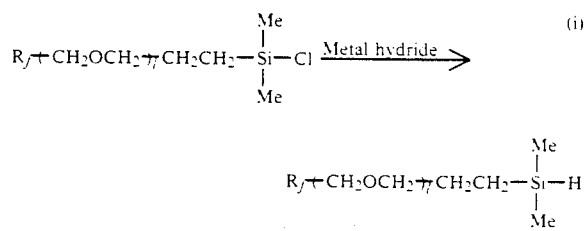

In the case n=2 or 3 in the formula [III], the organosilicon compound can be prepared similarly to the above using a corresponding dichlorosilane or tricholrosilane.

On the other hand, the organosilicon compound of the above formula [III] wherein m is 1 can be prepared, for instance in the case of n=1, by the partial addition reaction between 1,1,3,3-tetramethyldisiloxane and an olefin having a perfluoroalkyl group as a substituent as shown by the following reaction scheme (ii):

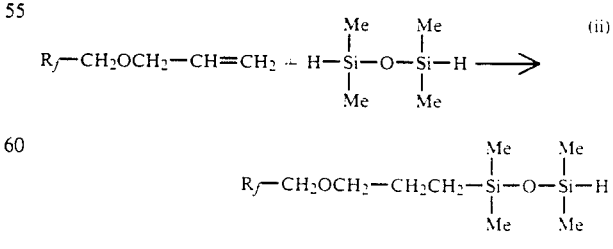

In the case n=2 or 3 in the formula [III], the organosilicon compound can be prepared similarly to the above using a corresponding trisiloxane or tetrasiloxane in place of said disiloxane.

Also, as shown by the following reaction scheme (iii), it can be prepared by the equilibration reaction of two kinds of disiloxane.

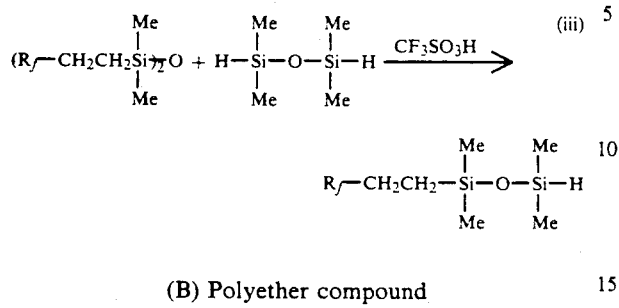

(B) Polyether compound

The other starting material to be used in the production process of the present invention is a polyether compound represented by the above formula [IV], namely:

$$CH_2=CH-CH_2O-Q-R \quad [IV]$$

wherein Q and R are the same as defined above.

In said formula [IV], the polyether group Q comprises one or more kinds of polyethylene glycol chains and/or polypropylene glycol chains as a constituent. More specifically, the polyether group Q may be either one of homopolymer chains of ethylene glycol, homopolymer chains of propylene glycol and copolymer chains of the both. And, where it consists of a copolymer chain of the both, either form of block polymer chain or random polymer chain may be employed. However, since the polyether group Q is introduced for the purpose of imparting hydrophilic nature to the surfactant, its polymerization degree is required to be determined in view of the balance with the organosilicon compound (A) having the fluorine-containing organic group $R_f$, i.e., the hydrophobic groups described above. For example, since propylene glycol is relatively lower in hydrophilic nature as compared with ethylene glycol, when a monopolymer chain of propylene grlycol is used as the polyether group Q, it is desirable to use a polymer chain with a relatively higher polymerization degree. On the other hand, when a copolymer chain of ethylene glycol and propylene glycol is used, the content of propylene glycol occupied in the whole may be preferably within the range from 2 to 10 mol %.

In the above formula [IV], if the terminal group R is an excessively large organic group, it may sometimes function as a hydrophobic group, whereby hydrophilic nature of the compound (B) may be damaged. Therefore, as the R, for example, an hydrogen atom, the allyl group, an alkyl group having 1 to 4 carbon atoms, or an acyl group having 2 to 4 carbon atoms is used. Among them, the methyl group and acetyl group are preferred. Where the terminal end R is allyl group, the compound (B) has a structure having allyl groups at both terminal ends, and the organosilicon compound (A) will react with these both terminal ends. In this case, it is desirable to use one wherein n is 1 in the above formula [III], namely one having one Si—H group, as the above organosilicon compound (A). If the reaction is carried out as described above by use of an organosilicon compound having 2 or more Si—H groups, there is a fear that the fluorine-containing organosilicon compound may be polymerized to become one unsuitable as the surfactant.

Non-limitative specific examples of the polyether compound as described above may include the following compounds:

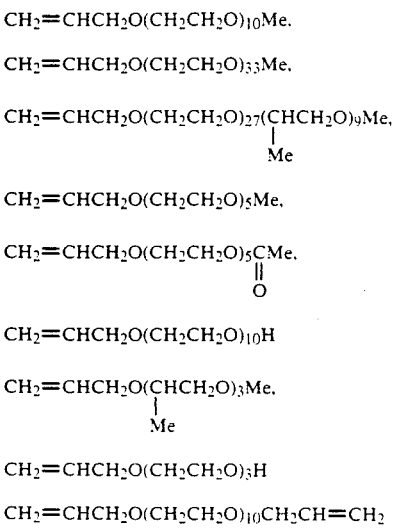

Reaction

According to the production process of the present invention, the desired fluorine-containing surfactant can be obtained by carrying out hydrosilylation reaction between the organosilicon compound (A) and the polyether compound (B) as described above in the presence of a platinum catalyst, so that the Si—H group of said compound (A) is added to the allyl group of the compound (B).

The platinum catalyst to be used in this reaction is not particularly limited, and includes, for example, chloroplatinic acid, alcohol-modified chloroplatinic acid, platinum-vinylsiloxane complexes, platinum black, complex of chloroplatinic acid with an olefin or an aldehyde. Particularly preferred are chloroplatinic acid, alcohol-modified chloroplatinic acid, and platinum-vinylsiloxane complex in view of their high activity. Such platinum catalysts may be generally used in an amount of about 1 to 100 ppm in terms of platinum based on the whole reaction mixture.

The reaction temperature may be 90° to 140° C. preferably 100° to 120° C., and the starting materials are generally diluted with a solvent for the reaction. The solvent to be used is not particularly limited, provided that it will not react with the Si—H group or allyl group when permitted to coexist with the platinum catalyst The solvent which may be used includes, for example, hydrocarbons such as benzene, toluene, xylene, hexane, heptane, octane, cyclohexane and the like; ethers such as diisopropyl ether, dibutyl ether and the like; siloxanes such as hexamethyldisiloxane, 1,1,3,3,5,5,7,7-octamethylcyclotetrasiloxane and the like. Where the viscosity of the starting materials and the reaction product are sufficiently low to cause no trouble in stirring, no solvent may be employed.

Fluorine-containing surfactant

The fluorine-containing surfactant of the present invention thus produced essentially consists of at least one fluorine-containing organosilicon compound selected from the group consisting of the compounds represented by the above formula [I] and [II].

Here, those represented by the above formula [I] are produced by use of those having the allyl group at one end of the molecular chain as the polyether compound (B). Typical examples of such fluorine-containing surfactants of the present invention includes the following fluorine-containing organosilicon compounds:
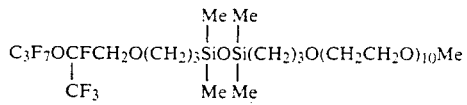
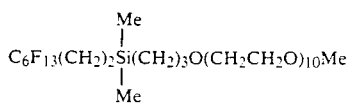
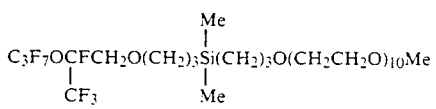
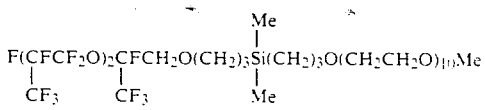
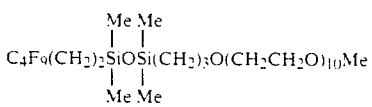
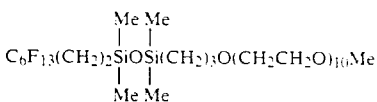
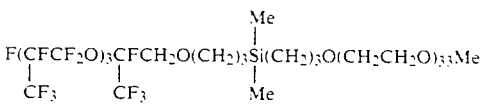
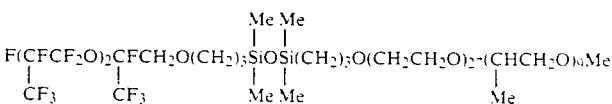
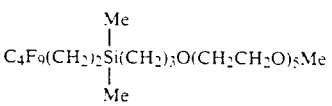
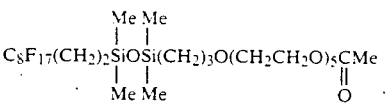
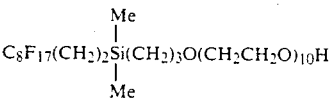
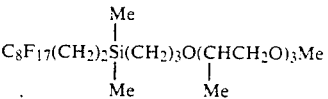
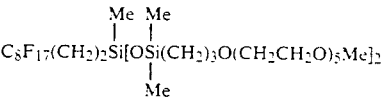
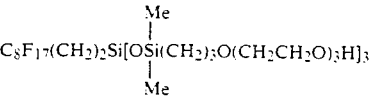

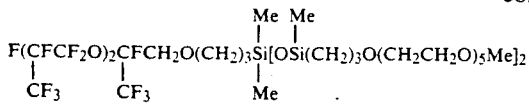

The fluorine-containing surfactants consisting of the fluorine-containing organosilicon compounds of the above formula [II] can be produced by using those having the allyl group at both ends of the molecular chain as the polyether compound (B) and using those with n=1 in the above formula [III], namely having one Si—H group, as the organosilicon compound (A). The fluorine-containing surfactant of this type includes the following compounds:

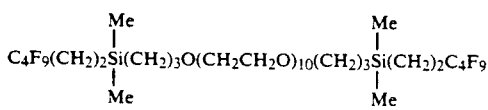

Since the novel fluorine-containing surfactant thus obtained has the properties of imparting or improving wettability, penetrability, spreadability, foam stability, flowability, emulsifiability, dispersibility, and water and oil repellency, applications in various fields can be expected. Specifically, the fluorine-containing surfactant may be applied to emulsifiers for polymerization, stabilizers of latex, preparation aids of agglomerated products of powdery fluorocarbon polymers, foaming additives for controlling unevenness of spreading and coating, additives for imparting water and oil repellent properties to grease, and inner antistatic agents and antitack agents in polyolefins in the field of plastic and rubber industries; additives for improvement of flowability during recovery of heavy oil from storage device, additives for improvement of abrasion resistance of lubricant oils, additives for prevention of freezing in gasifier of gasoline, and evaporation inhibitor of gasoline or jet fuel by film formation in the field of petrochemical industries; additives for improvement of flowability for improving the melting prevention step, carbonization aid of wool, additives for lowering surface tension of a synthetic paste, aqueous PVA solution, in the spinning sizing step, mercerization aids, and dye finishing aids in the field of textile industries; aids for improvement of coloring power and dispersibility of pigments, agents for imparting flow leveling and sink prevention for correcting paint defects, and controllers of evaporation rate of the solvent in the paint in the field of dye and pigment industries; additives for the luster treatment bath, additives for etching metals, additives for solder flux, corrosion inhibitor, and mist preventing agents for plating in the field of metal and mechanical industries; penetration improvers of fungicides, wettability improvers of herbicides and insecticides, and improvers of emulsifiability, dispersibility and spreadability in the field of pharmaceuticals and agricultural chemicals; additives for cleaning agents, leveling improvers for polish, additives for cosmetics, and antistatic agents in the field of household goods; additives for imparting flowability and flow leveling of ink, leveling agents for photographic emulsions, antistatic agents for films, and film drying accelerators, etc. in the field of photography and printing; etc.

EXAMPLES

Example 1

A four-necked flask was charged with 51 g (0.1 mol) of a polyethylene oxide with an average polymerization degree of 10 having the allyl group and the methyl group at each terminal end and 100 ml of toluene, and 5 ml of toluene containing 0.07 g of a chloroplatinic acid was added thereto, followed by heating at 100° to 110° C. Under stirring of the contents in the flask, 53 g (0.105 mol) of 2-(heptadecafluorooctylethyl)-dimethylsilane was added dropwise thereto. After the addition, reaction was carried out at 110° to 120° C. for about 5 hours. After confirmation of the amount of the silane consumed by gas chromatography, toluene and low boiling distillates were removed from the reaction mixture at 130°-150° C./5 mm Hg. As the result, 92 g of brown liquid was obtained. When the IR spectrum of this product was measured, absorptions due to the Si—H group at 2250 cm$^{-1}$ and the allyl group at 1630 cm$^{-1}$ were found to have disappeared, whereby the progress of the reaction could be confirmed. Further, although the polyether and the fluorine-containing silane of the starting materials are not compatible with each other, the reaction mixture was a uniform liquid. From this fact, the product obtained was confirmed to be the desired compound of:

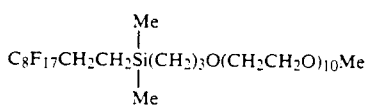

Yield: 84%.

EXAMPLES 2-17

The reactions were carried out according to the same method as in the above Example 1 except for changing variously the polyether compound and the fluorine-containing organosilicon compound as shown in Table 1 to obtain various fluorine-containing surfactants. The starting materials, the products and the yields in the respective Examples are shown in Table 1.

Evaluation of the fluorine-containing surfactant

Surface tensions of the aqueous solutions of the surfactants obtained in Examples 1 to 17 were measured at various concentrations of the surfactants. The results are shown in Table 2. For measurement of surface tension, the Wilhelmi method was employed, at 25° C., by use of a glass plate being as the objective material.

TABLE 1

| Example No. | Raw materials Silane or siloxane | Polyether | Products Structure | Yield (%) |
|---|---|---|---|---|
| 2 | $C_3F_7OCFCH_2O(CH_2)_3SiH$<br>$\quad \mid \qquad \qquad \mid \quad \mid$<br>$\quad CF_3 \qquad \quad Me\ Me$ | $CH_2=CHCH_2O(CH_2CH_2O)_{10}Me$ | $\quad\quad\quad\quad Me\ Me$<br>$C_3F_7OCFCH_2O(CH_2)_3SiOSi(CH_2)_3O(CH_2CH_2O)_{10}Me$<br>$\quad \mid \qquad\qquad\qquad \mid \quad \mid$<br>$\quad CF_3 \qquad\qquad\quad Me\ Me$ | 91 |
| 3 | $\quad\quad Me$<br>$C_6F_{13}(CH_2)_2SiH$<br>$\quad\quad \mid$<br>$\quad\quad Me$ | " | $\quad\quad Me$<br>$C_6F_{13}(CH_2)_2Si(CH_2)_3O(CH_2CH_2O)_{10}Me$<br>$\quad\quad \mid$<br>$\quad\quad Me$ | 87 |
| 4 | $C_3F_7OCFCH_2O(CH_2)_3SiH$<br>$\quad \mid \qquad\qquad \mid$<br>$\quad CF_3 \qquad\quad Me$<br>$\quad\quad\quad\quad\quad\quad\quad Me$ | " | $C_3F_7OCFCH_2O(CH_2)_3Si(CH_2)_3O(CH_2CH_2O)_{10}Me$<br>$\quad \mid \qquad\qquad\qquad \mid$<br>$\quad CF_3 \qquad\qquad\quad Me$<br>$\quad\quad\quad\quad\quad\quad\quad\quad\quad\quad\quad Me$ | 89 |
| 5 | $F(CFCF_2O)_3CFCH_2O(CH_2)_3SiH$<br>$\quad\ \mid \qquad\qquad \mid \qquad \mid$<br>$\quad CF_3 \qquad\ \  CF_3 \quad Me\ Me$ | " | $\quad\quad\quad\quad\quad\quad\quad\quad\quad\quad Me$<br>$F(CFCF_2O)_3CFCH_2O(CH_2)_3Si(CH_2)_3O(CH_2CH_2O)_{10}Me$<br>$\quad\ \mid \qquad\qquad\ \ \mid \qquad \mid$<br>$\quad CF_3 \qquad\quad CF_3 \quad Me$ | 88 |
| 6 | $\quad\quad\quad\quad\ \ Me\ Me$<br>$C_4F_9(CH_2)_3SiOSiH$<br>$\quad\quad\quad\quad \mid \quad \mid$<br>$\quad\quad\quad\quad Me\ Me$ | " | $\quad\quad\quad\quad\ Me\ Me$<br>$C_4F_9(CH_2)_3SiOSi(CH_2)_3O(CH_2CH_2O)_{10}Me$<br>$\quad\quad\quad\quad \mid \quad \mid$<br>$\quad\quad\quad\quad Me\ Me$ | 90 |
| 7 | $\quad\quad\quad\quad\ \ Me\ Me$<br>$C_6F_{13}(CH_2)_2SiOSiH$<br>$\quad\quad\quad\quad \mid \quad \mid$<br>$\quad\quad\quad\quad Me\ Me$ | " | $\quad\quad\quad\quad\ Me\ Me$<br>$C_6F_{13}(CH_2)_2SiOSi(CH_2)_3O(CH_2CH_2O)_{10}Me$<br>$\quad\quad\quad\quad \mid \quad \mid$<br>$\quad\quad\quad\quad Me\ Me$ | 89 |
| 8 | $F(CFCF_2O)_3CFCH_2O(CH_2)_3SiH$<br>$\quad\ \mid \qquad\qquad \mid \qquad \mid$<br>$\quad CF_3 \qquad\ \  CF_3 \quad Me$<br>$\quad\quad\quad\quad\quad\quad\quad\quad\quad\quad\quad Me$ | $CH_2=CHCH_2O(CH_2CH_2O)_{13}Me$ | $\quad\quad\quad\quad\quad\quad\quad\quad\quad\quad Me$<br>$F(CFCF_2O)_3CFCH_2O(CH_2)_3Si(CH_2)_3O(CH_2CH_2O)_{13}Me$<br>$\quad\ \mid \qquad\qquad\ \ \mid \qquad \mid$<br>$\quad CF_3 \qquad\quad CF_3 \quad Me$ | 91 |
| 9 | $F(CFCF_2O)_3CFCH_2O(CH_2)_3SiOSiH$<br>$\quad\ \mid \qquad\qquad \mid \qquad \mid \quad \mid$<br>$\quad CF_3 \qquad\ \  CF_3 \quad Me\ Me\ Me$ | $CH_2=CHCH_2O(CH_2CH_2O)_{27}(CHCH_2O)_9Me$<br>$\qquad\qquad\qquad\qquad\qquad\qquad\qquad \mid$<br>$\qquad\qquad\qquad\qquad\qquad\qquad\qquad Me$ | $\quad\quad\quad\quad\quad\quad\quad\quad\quad\quad Me\ Me$<br>$F(CFCF_2O)_3CFCH_2O(CH_2)_3SiOSi(CH_2)_3O(CH_2CH_2O)_{27}(CHCH_2O)_9Me$<br>$\quad\ \mid \qquad\qquad\ \ \mid \qquad \mid \quad \mid \qquad\qquad\qquad\qquad\qquad \mid$<br>$\quad CF_3 \qquad\quad CF_3 \quad Me\ Me\qquad\qquad\qquad\qquad\qquad Me$ | 98 |
| 10 | $\quad\quad Me$<br>$C_4F_9(CH_2)_2SiH$<br>$\quad\quad \mid$<br>$\quad\quad Me$ | $CH_2=CHCH_2O(CH_2CH_2O)_5Me$ | $\quad\quad Me$<br>$C_4F_9(CH_2)_2Si(CH_2)_3O(CH_2CH_2O)_5Me$<br>$\quad\quad \mid$<br>$\quad\quad Me$ | 80 |

TABLE 1-continued

| Example No. | Raw materials | | Products | | Yield (%) |
|---|---|---|---|---|---|
| | Silane or siloxane | Polyether | Structure | | |
| 11 | $C_8F_{17}(CH_2)_2SiOSiH$ with Me,Me,Me,Me groups | $CH_2=CHCH_2O(CH_2CH_2O)_5CMe=O$ | $C_8F_{17}(CH_2)_2SiOSi(CH_2)_3O(CH_2CH_2O)_5CMe=O$ with Me,Me,Me,Me | | 82 |
| 12 | $C_8F_{17}(CH_2)_2SiH$ with Me,Me | $CH_2=CHCH_2O(CH_2CH_2O)_{10}H$ | $C_8F_{17}(CH_2)_2Si(CH_2)_3O(CH_2CH_2O)_{10}H$ with Me,Me | | 90 |
| 13 | " | $CH_2=CHCH_2O(CHCH_2O)_3Me$ with Me | $C_8F_{17}(CH_2)_2Si(CH_2)_3O(CHCH_2O)_3Me$ with Me,Me,Me | | 94 |
| 14 | $C_8F_{17}(CH_2)_2Si(OSiH)_2$ with Me,Me,Me | $CH_2=CHCH_2O(CH_2CH_2O)_5Me$ | $C_8F_{17}(CH_2)_2Si\{OSi(CH_2)_3O(CH_2CH_2O)_5Me\}_2$ with Me groups | | 98 |
| 15 | $C_8F_{17}(CH_2)_2Si(OSiH)_3$ with Me | $CH_2=CHCH_2O(CH_2CH_2O)_3H$ | $C_8F_{17}(CH_2)_2Si\{OSi(CH_2)_3O(CH_2CH_2O)_3H\}_3$ with Me,Me | | 93 |
| 16 | $F(CFCF_2O)_2CFCH_2O(CH_2)_3Si(OSiH)_2$ with $CF_3$,$CF_3$,Me,Me | $CH_2=CHCH_2O(CH_2CH_2O)_5Me$ | $F(CFCF_2O)_2CFCH_2O(CH_2)_3Si\{OSi(CH_2)_3O(CH_2CH_2O)_5Me\}_2$ with $CF_3$,$CF_3$,Me,Me | | 88 |
| 17 | $C_4F_9(CH_2)_2SiH$ with Me,Me | $CH_2=CHCH_2O(CH_2CH_2O)_{10}CH_2CH=CH_2$ | $C_4F_9(CH_2)_2Si(CH_2)_3O(CH_2CH_2O)_{10}(CH_2)_3Si(CH_2)_2C_4F_9$ with Me,Me,Me,Me | | 85 |

TABLE 2

| Example | Surface tension (dyn/cm) Surfactant concentration | |
| --- | --- | --- |
| | 0.1 (w/v %) | 0.01 (w/v %) |
| 1 | 20.8 | 22.9 |
| 2 | 19.5 | 20.6 |
| 3 | 21.1 | 21.6 |
| 4 | 20.4 | 20.8 |
| 5 | 19.3 | 25.4 |
| 6 | 20.4 | 20.6 |
| 7 | 20.5 | 22.9 |
| 8 | 35.7 | 49.0 |
| 9 | 31.5 | 34.0 |
| 10 | 20.2 | 20.5 |
| 11 | 27.4 | 49.0 |
| 12 | 22.0 | 36.0 |
| 13 | 41.1 | 55.6 |
| 14 | 22.9 | 24.0 |
| 15 | 23.7 | 38.8 |
| 16 | 22.5 | 25.3 |
| 17 | 24.3 | 29.0 |

(Remarks)
Surface tension of water: 72.4 dyn/cm

I claim:

1. A fluorine-containing surfactant essentially consisting of at least one compound selected from the group consisting of:
fluorine-containing silicon compounds of the formula [I]:

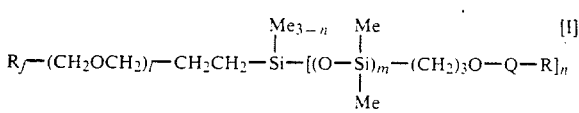

wherein
  $R_f$ represents a perfluoroalkyl group having 4 to 10 carbon atoms or a perfluoropolyether group having 5 to 14 carbon atoms;
  Q represents a polyether group consisting of a polyethylene glycol chain, a polypropylene glycol chain or an admixture thereof;
  R represents a hydrogen atom, the allyl group, an alkyl group having 1 to 4 carbon atoms, or an acyl group having 2 to 3 carbon atoms;
  l and m are each an integer of 0 or 1, and n is an integer of 1 to 3, and
fluorine-containing silicon compounds of the formula [II]:

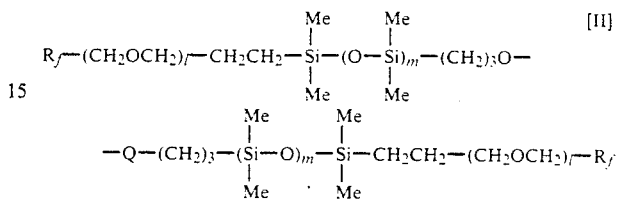

wherein Rf, Q, l and m are the same as defined above.

2. The fluorine-containing surfactant according to claim 1, wherein, in said formula [I] and/or [II], $R_f$ is a perfluoroalkyl group having 4 to 10 carbon atoms, and l is 0.

3. The fluorine-containing surfactant according to claim 1, wherein, in said formula [I] and/or [II], $R_f$ is a perfluoroether group having 5 to 14 carbon atoms, and l is 1.

4. The fluorine-containing surfactant according to claim 3, wherein said perfluoropolyether group has a group represented the formula:

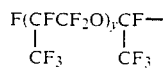

where y is an integer of 1 to 4.

* * * * *